(12) United States Patent
Yao

(10) Patent No.: US 10,569,103 B2
(45) Date of Patent: Feb. 25, 2020

(54) GRATING DEVICE FOR RADIOTHERAPY EQUIPMENT, CONTROL METHOD THEREOF AND RADIOTHERAPY EQUIPMENT

(71) Applicant: SUZHOU LINATECH MEDICAL SCIENCE AND TECHNOLOGY CO., LTD., Industry Park Suzhou, Jiangsu (CN)

(72) Inventor: Jonathan Yi Yao, Jiangsu (CN)

(73) Assignee: SUZHOU LINATECH MEDICAL SCIENCE AND TECHNOLOGY CO., LTD., Jiangsu (CN)

(*) Notice: Subject to any disclaimer, the term of this patent is extended or adjusted under 35 U.S.C. 154(b) by 200 days.

(21) Appl. No.: 15/552,571

(22) PCT Filed: Apr. 5, 2016

(86) PCT No.: PCT/CN2016/078419
§ 371 (c)(1),
(2) Date: Aug. 22, 2017

(87) PCT Pub. No.: WO2016/161923
PCT Pub. Date: Oct. 13, 2016

(65) Prior Publication Data
US 2018/0043187 A1 Feb. 15, 2018

(30) Foreign Application Priority Data
Apr. 8, 2015 (CN) .......................... 2015 1 0161364

(51) Int. Cl.
*A61N 5/10* (2006.01)
*A61B 6/02* (2006.01)
(Continued)

(52) U.S. Cl.
CPC .............. *A61N 5/1048* (2013.01); *A61B 6/02* (2013.01); *A61N 5/1001* (2013.01); *A61B 5/055* (2013.01);
(Continued)

(58) Field of Classification Search
CPC ..... A61B 2505/05; A61B 5/055; A61B 5/704; A61B 6/02; A61N 2005/0626;
(Continued)

(56) References Cited

U.S. PATENT DOCUMENTS

2009/0080619 A1* 3/2009 Hasegawa ................ G21K 1/04
378/151
2009/0095921 A1 4/2009 Bert et al.
(Continued)

FOREIGN PATENT DOCUMENTS

CN 101364453 A 2/2009
CN 202777469 U 3/2013
(Continued)

*Primary Examiner* — Marcus H Taningco
(74) *Attorney, Agent, or Firm* — Muncy, Geissler, Olds & Lowe, P.C.

(57) ABSTRACT

The invention discloses a grating device for radiotherapy equipment. A tail-end position controller and a front-end position controller are simultaneously arranged, and can simultaneously verify a tail-end position and a middle position of each single grating blade and measure the time during which one grating blade arrives at the middle position from the tail-end position and/or the total number of revolutions of a motor at any time. Because the distance between the tail-end position and the middle position is fixed and can be accurately measured, the system can accurately verify the position of one grating blade and control the grating blades to arrive at an accurately specified position; because the grating blades can be conveniently verified and controlled one by one, transmission errors caused by different grating blade driving systems and errors caused by instable performance can be effectively overcome; even verification can be performed before each fitting of a radiation field, and then accurate control can be realized according to the latest measured actual parameters.

10 Claims, 3 Drawing Sheets

(51) Int. Cl.
 *A61B 5/055* (2006.01)
 *A61N 5/06* (2006.01)
(52) U.S. Cl.
 CPC .............. *A61N 2005/0626* (2013.01); *A61N 2005/1092* (2013.01)
(58) Field of Classification Search
 CPC .... A61N 2005/1092; A61N 2005/1095; A61N 5/1001; A61N 5/1045; A61N 5/1048
 See application file for complete search history.

(56) References Cited

U.S. PATENT DOCUMENTS

2013/0284951 A1* 10/2013 Echner ................. A61N 5/1045
 250/505.1
2017/0202528 A1* 7/2017 Roessl ..................... G21K 1/06

FOREIGN PATENT DOCUMENTS

| CN | 103537009 A | 1/2014 |
|----|-------------|--------|
| CN | 204134059 U | 2/2015 |
| CN | 104759032 A | 7/2015 |
| CN | 204582310 U | 8/2015 |

\* cited by examiner

GRATING DEVICE FOR RADIOTHERAPY EQUIPMENT, CONTROL METHOD THEREOF AND RADIOTHERAPY EQUIPMENT

FIELD OF THE INVENTION

The invention relates to a grating device for radiotherapy equipment, a control method thereof and radiotherapy equipment.

BACKGROUND OF THE INVENTION

Radiotherapy equipment has been widely applied, wherein the grating blade device for fitting the shape of a lesion and defining a radiation field of rays has been greatly developed. The structural shape of blades, the arrangement of blades and the precision of fitting the radiation field are all continuously improved. However, in the prior art, the control on accurate positions of grating blades driven by a motor is difficult to master, and a motor driving system itself has natural defects, e.g., transmission error of the screw, instability of the motor, etc., so that the precision of fitting the radiation field cannot be further improved and the verification of the equipment is very complicated and difficult.

SUMMARY OF THE INVENTION

To solve the above problems, the present invention is aimed at providing a grating device which is simple in verification and can improve the radiation field fitting precision, a control method thereof and radiotherapy equipment.

To fulfill the above aim, the present invention adopts the following technical solution:

a grating device for radiotherapy equipment, comprising grating blades and a driving device thereof, and further comprising:

a tail-end position controller, used for monitoring whether the tail ends of the grating blades arrive at a preset zero position, i.e., an initial position; and a front-end position controller, used for monitoring whether the front ends of the grating blades arrive at the middle position, wherein when the two groups of grating blades are at the initial position, front-end projections of the two groups of grating blades are two parallel straight lines, and the middle position is a straight line equidistant from the front ends of the two groups of grating blades.

The tail-end position controller and the front-end position controller are simultaneously arranged, and can simultaneously verify the tail-end position and the middle position of a single grating blade and measure the time during which one grating blade arrives at the middle position from the tail-end position and/or the total number of revolutions of a motor at any time. Because the distance between the tail-end position and the middle position is fixed and can be accurately measured, the system can accurately verify the position of one grating blade and control the grating blades to arrive at an accurately specified position; because the grating blades can be conveniently verified and controlled one by one, transmission errors caused by different grating blade driving systems and errors caused by instable performance can be effectively overcome; even verification can be performed before each fitting of a radiation field, and then accurate control can be realized according to the latest measured actual parameters.

Further, the grating device for radiotherapy equipment is also provided with a central controller, the central controller is connected with the driving device, the tail-end position controller and the front-end position controller respectively, the central controller receives data transmitted from the tail-end position controller and the front-end position controller, makes a judgment hereby and sends a control instruction to the driving device, and the driving device controls the grating blades to move or stop.

Further, front-end position sensors are arranged at the front ends, i.e., the free ends, of the grating blades, and the front-end position sensors are triggered when the front ends of the two corresponding grating blades in the two groups of grating blades touch each other.

Further, front-end position sensors matched with each other are respectively arranged at the front end, i.e., the free end, of each grating blade and a position corresponding to a middle line in the grating device, and the front-end position sensors are triggered when the front end of one grating blade arrives at the middle line.

Further, a transverse through-hole is formed in the front end of each grating blade of the grating device, a moving part of the front-end position sensor is arranged in the through-hole, a fixed part of the front-end position sensor is arranged on a grating blade support on one side or two sides of the grating blade, and when the moving part and fixed part of the front-end position sensor on one grating blade are located on the same straight line and trigger the front-end position sensor, the front end of the grating blade is just located on the middle line.

Further, the front-end position controller comprises:

a driving part, which is arranged on a grating body and drives limiting rods to stretch and contract horizontally;

two limiting rods, which can independently horizontally stretch and contract along the middle line and respectively correspond to the two groups of grating blades of the grating device; and front-end position sensors, which are arranged on the limiting rods and face one side of the front ends of the grating blades, wherein after the limiting rods completely move to a work area of the grating blades, the front-end position sensors correspond to all the grating blades one by one; after one grating blade touches the front-end position sensor corresponding thereto, the front-end position sensor is triggered, and the front end of the grating blade is located on the middle line at the moment.

The present invention further provides a control method for the grating device for radiotherapy equipment, comprising but not limited to the following working conditions:

initial position verification: when initial position sensors are independently arranged for each grating blade through a tail-end controller, the initial position verification method is to independently verify the initial position of each grating blade according to the detection data of each initial position sensor or control all or part of the grating blades to return to the initial position simultaneously or respectively; when only one initial position sensor is arranged for each group of grating blades, the initial position verification method comprises the steps of driving all the grating blades to leave from the initial position first, then moving the first grating blade which needs to be verified to the initial position till triggering the initial position sensor, marking the initial position to complete the initial position verification of the first grating blade, then driving the grating blade to leave from the initial position, and verifying the initial position of the second grating blade according to the same program till completing the initial position verification of all the grating blades;

middle position verification: the middle position verification method comprises the steps of arranging a middle position sensor at the middle position as described in claim 1, driving all the grating blades to leave from the middle position first, then moving the first grating blade which needs to be verified to the middle position till triggering the middle position sensor, marking the middle position to complete the middle position verification of the first grating blade, driving the grating blade to leave from the middle position, and then verifying the middle position of the second grating blade according to the same program till completing the middle position verification of all the grating blades; and precise positioning of the grating blades: the precise positioning method of the grating blades comprises the following steps: step 1, completing the initial position verification and the middle position verification, and obtaining the distance L between the initial position and the middle position as known or actually measured; step 2, driving one grating blade to move from the initial position to the middle position or from the middle position to the initial position, and recording the running time T or the motor revolution number S; step 3, driving the grating blade to return to the initial position, and marking the initial position as zero at the moment; and step 4, driving the grating blade to move from the initial position to the middle position, and simultaneously recording the time t or the revolution number s, the real-time position, i.e., actual moving distance, of the grating blade being $l=Lt/T$ or $l=Ls/S$, and when l is equal to a preset value or a required value, the grating blade arriving at a target position and stopping moving.

Further, the control method also comprises but not limited to the following working condition:

front-end position verification: the so-called front-end position means that when one grating blade in one of the two groups of grating blades is at the initial position, the position of the end face, close to one side of the middle position, i.e., the end surface of the free end, of the grating blade is a front-end position of a grating blade corresponding to the grating blade in the other group of grating blades, i.e., an extreme position at which one grating blade can move forward; the front-end position verification method comprises the steps of arranging front-end position sensors at the front ends, i.e., the free ends, of the grating blades, driving single grating blades in one group of grating blades or in the other group at the position corresponding to the grating blades to be verified to return to the initial position first, then moving the first grating blade which needs to be verified to the front-end position till triggering the front-end position sensor, marking the front-end position to complete the front-end position verification of the first grating blade, and then verifying the front-end position of the second grating blade according to the same program till completing the front-end position verification of all the grating blades.

Further, the control method also comprises but not limited to the following working condition:

moving speed verification of the grating blades or parameter verification of the motor, comprising the following steps: step 1, completing the initial position verification and the middle position verification, and obtaining the distance L between the initial position and the middle position as known or actually measured; step 2, driving one grating blade to move from the initial position to the middle position or from the middle position to the initial position, and recording the running time T or the motor revolution number S; and step 3, comparing the measured running time T or motor revolution number S with the previously stored running time T or motor revolution number S, if they are the same, prompting they are the same, and if they are different, executing at least one of the following steps: 1) prompting they are different, 2) repeating the above steps after adjustment or maintenance, and 3) storing the newly measured running time T or motor revolution number S, and incorporating the newly measured running time T or motor revolution number S into the technical formula $l=Lt/T$ or $l=Ls/S$ of the real-time position instead of the original parameters.

The present invention further provides radiotherapy equipment, comprising a large frame and an accelerator arranged on the large frame, and also comprising the above-mentioned grating device.

Figure 1:
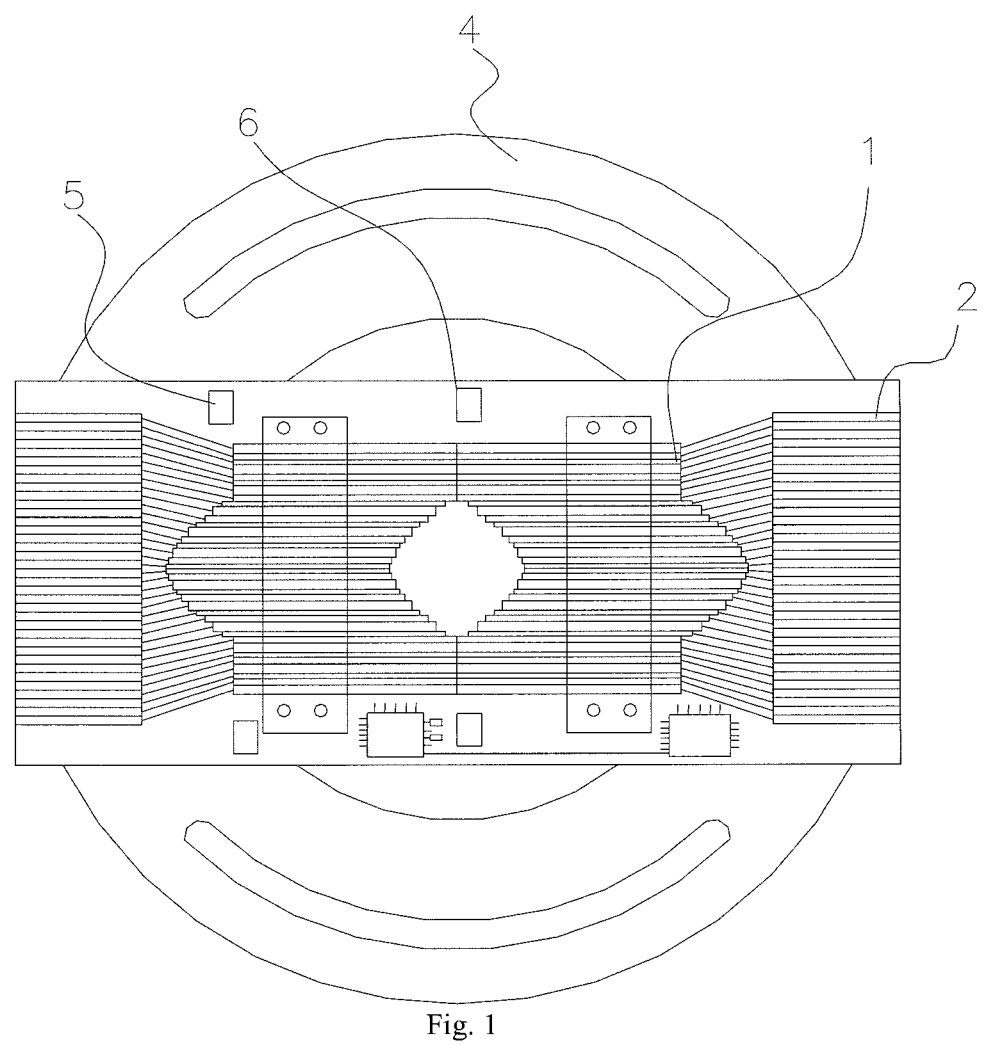
FIGS. 1 and 2 are schematic diagrams of the present invention.

Numbers and letters in the drawings express corresponding components:

1, grating blade; 2, driving device; 4, adapter; 5, tail-end position controller; 6, front-end position controller; 7, large frame; 8, accelerator; 9, light limiting barrel support; 91, light limiting barrel; 10, grating device; 20, therapy bed; 61, driving part; 62, limiting rod.

DETAILED DESCRIPTION OF THE EMBODIMENTS

The present invention will be further described in detail below in combination with the accompanying drawings and specific embodiments.

Figure 2:
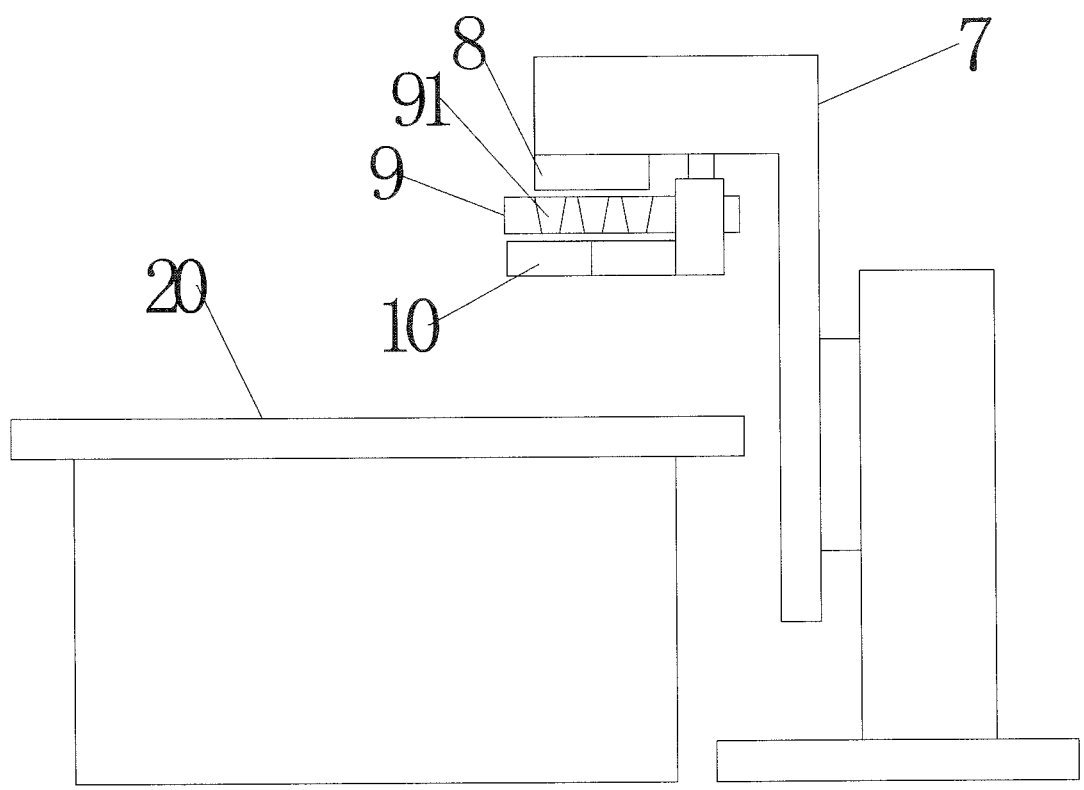

One embodiment shown in FIGS. 1 and 2 shows a grating device 10 for radiotherapy equipment. The grating device 10 comprises grating blades 1 and a driving device 2 thereof, and further comprises:

a tail-end position controller 5, used for monitoring whether the tail ends of the grating blades 1 arrive at a preset zero position, i.e., an initial position; and a front-end position controller 6, used for monitoring whether the front ends of the grating blades 1 arrive at the middle position, wherein when the two groups of grating blades 1 are at the initial position, front-end projections of the two groups of grating blades 1 are two parallel straight lines, and the middle position is a straight line equidistant from the front ends of the two groups of grating blades.

In FIG. 2, the radiotherapy equipment generally comprises a large frame 7, an accelerator 8, the grating device 10 and a therapy bed 20; a light limiting barrel support 9 and light limiting barrels 91 are optional; when a patient is treated, relative movement of the grating blades 1 on two sides of the grating device is controlled according to the shape and size of a lesion, and the front ends of the grating blades cooperate with each other to fit the shape of the lesion to form a window for controlling a ray radiation field of the accelerator, as shown in FIG. 1. The tail-end position controller 5 and the front-end position controller 6 are simultaneously arranged, and can simultaneously verify the tail-end position and the middle position of a single grating blade 1 and measure the time during which one grating blade 1 arrives at the middle position from the tail-end position and/or the total number of revolutions of a motor at any time. Because the distance between the tail-end position and the middle position is fixed and can be accurately measured, the system can accurately verify the position of one grating blade 1 and control the grating blade 1 to arrive at an accurately specified position; because the grating blades 1 can be conveniently verified and controlled one by one, transmission errors caused by different grating blade driving systems and errors caused by instable performance can be effectively overcome; even verification can be performed before each fitting of a radiation field, and then accurate control can be realized according to the latest measured actual parameters.

In practical application, the control system can be realized by adopting multiple control systems in the prior art, or a central controller is arranged in the grating device for radiotherapy equipment, the central controller is connected with the driving device 2, the tail-end position controller 5 and the front-end position controller 6 respectively, the central controller receives data transmitted from the tail-end position controller 5 and the front-end position controller 6, makes a judgment and sends a control instruction to the driving device, and the driving device 2 controls the grating blades 1 to move or stop.

In practical application, the tail-end position controller 5 and the front-end position controller 6 can be electromagnetic sensors, micro switches, photoelectric sensors or other similar devices for detecting whether the front ends and the tail ends of the grating blades 1 arrive at a specific position, e.g., a reference line sensor can be arranged at the initial position of the tail ends of the grating blades, or a sensor or detection switch is arranged in correspondence to each grating blade. When initial position sensors are independently arranged for each grating blade through the tail-end controller, the initial position verification method is to independently verify the initial position of each grating blade according to the detection data of each initial position sensor or control all or part of the grating blades to return to the initial position simultaneously or respectively; when only one initial position sensor is arranged for each group of grating blades, the initial position verification method comprises the steps of driving all the grating blades to leave from the initial position first, moving the first grating blade which needs to be verified to the initial position till triggering the initial position sensor, marking the initial position to complete initial position verification of the first grating blade, driving the grating blade to leave from the initial position, and then verifying the initial position of the second grating blade according to the same program till completing the initial position verification of all the grating blades.

In order to verify whether one grating blade 1 arrives at the middle position, the time during which the grating blade 1 arrives at the middle position from the initial position or the number of revolutions of a driving motor, a detection device for detecting whether one grating blade arrives at the middle position is needed, and both the initial position and the middle position are definite positions, so the distance between the initial position and the middle position can be premeasured and stored in the controller of the equipment; various sensors and micro switches may also be adopted in order to detect whether one grating blade arrives at the middle position, for example, the middle position verification method comprises the steps of arranging a middle position sensor (e.g., an infrared sensor, a laser sensor, etc.) at the middle position, driving all the grating blades to leave from the middle position first, then moving the first grating blade which needs to be verified to the middle position till triggering the middle position sensor, marking the middle position to complete the middle position verification of the first grating blade, driving the grating blade to leave from the middle position, and then verifying the middle position of the second grating blade according to the same program till completing the middle position verification of all the grating blades; next, precise positioning method of the grating blades: the precise positioning method of the grating blades comprises the following steps: step 1, completing the initial position verification and the middle position verification, and obtaining the distance L between the initial position and the middle position as known or actually measured; step 2, driving one grating blade to move from the initial position to the middle position or from the middle position to the initial position, and recording the running time T or the motor revolution number S; step 3, driving the grating blade to return to the initial position, and marking the initial position as zero at the moment; and step 4, driving the grating blade to move from the initial position to the middle position, and simultaneously recording the time t or the revolution number s, the real-time position, i.e., actual moving distance, of the grating blade being $l=Lt/T$ or $l=Ls/S$, when l is equal to a preset value or a required value, the grating blade arriving at a target position and stopping moving.

The technical solution provided by the present invention can also solve the following technical problems:

1. Front-end position verification: the so-called front-end position means that when one grating blade in one of the two groups of grating blades is at the initial position, the position of the end face, close to one side of the middle position, i.e., the end surface of the free end, of the grating blade is a front-end position of a grating blade corresponding to the grating blade in the other group of grating blades, i.e., an extreme position at which one grating blade can move forward; the front-end position verification method comprises the steps of arranging front-end position sensors at the front ends, i.e., the free ends, of the grating blades, driving single grating blades in one group of grating blades or in the other group at the position corresponding to the grating blades to be verified to return to the initial position first, then moving the first grating blade to be verified to the front-end position till triggering the front-end position sensor, marking the front-end position to complete the front-end position verification of the first grating blade, and then verifying the front-end position of the second grating blade according to the same program till completing the front-end position verification of all the grating blades.

2. Moving speed verification of the grating blades or parameter verification of the motor, comprising the following steps: step 1, completing the initial position verification and the middle position verification, and obtaining the distance L between the initial position and the middle position as known or actually measured; step 2, driving one grating blade to move from the initial position to the middle position or from the middle position to the initial position, and recording the running time T or the motor revolution number S; and step 3, comparing the measured running time T or motor revolution number S with the previously stored running time T or motor revolution number S, if they are the same, prompting they are the same, and if they are different, executing at least one of the following steps: 1) prompting they are different, 2) repeating the above steps after adjustment or maintenance, and 3) storing the newly measured running time T or motor revolution number S, and incorporating the newly measured running time T or motor revolution number S into the technical formula $l=Lt/T$ or $l=Ls/S$ of the real-time position instead of the original parameters.

The front-end position sensors may be arranged on two sides of the middle position of the two group of grating blades and may be infrared sensors or laser sensors or the like, i.e., the two groups of grating blades share one group of middle position sensors, and the middle positions of the grating blades need to be verified one by one. Or, a middle position detector is arranged on each grating blade, e.g., front-end position sensors (e.g., electromagnetic sensors or micro switches) are arranged at the front ends, i.e., the free ends, of the grating blades 1, and after the front ends of the two corresponding grating blades in the two group of grating blades touch each other, the front-end position sensors are triggered. In this case, a plurality of grating blades can be verified simultaneously.

The present invention further provides a control method for the grating device for radiotherapy equipment, comprising but not limited to the following working conditions:

initial position verification: when an initial position sensor is independently arranged for each grating blade through a tail-end controller, the initial position verification method is to independently verify the initial position of each grating blade according to the detection data of each initial position sensor or control part of or all of the grating blades to return to the initial position simultaneously or respectively; when only one initial position sensor is arranged for each group of grating blades, the initial position verification method comprises the steps of driving all the grating blades to leave from the initial position first, then moving the first grating blade which needs to be verified to the initial position till triggering the initial position sensor, marking the initial position to complete the initial position verification of the first grating blade, driving the grating blade to leave from the initial position, and then verifying the initial position of the second grating blade according to the same program till completing the initial position verification of all the grating blades.

middle position verification: the middle position verification method comprises the steps of arranging a middle position sensor at the middle position as described in claim 1, driving all the grating blades to leave from the middle position first, then moving the first grating blade which needs to be verified to the middle position till triggering the middle position sensor, marking the middle position to complete the middle position verification of the first grating blade, driving the grating blade to leave from the middle position, and then verifying the middle position of the second grating blade according to the same program till completing the middle position verification of all the grating blades, and precise positioning of the grating blades: the precise positioning method of the grating blades comprises the following steps: step 1, completing the initial position verification and the middle position verification, and obtaining the distance L between the initial position and the middle position as known or actually measured; step 2, driving one grating blade to move from the initial position to the middle position or from the middle position to the initial position, and recording the running time T or the motor revolution number S; step 3, returning the grating blade to the initial position, and marking the initial position as zero at the moment; and step 4, moving the grating blade from the initial position to the middle position, and simultaneously recording the time t or the revolution number s, the real-time position, i.e., actual moving distance, of the grating blade being $l=Lt/T$ or $l=Ls/S$, when l is equal to a preset value or a required value, the grating blade arriving at a target position and stopping moving.

Further, the control method also comprises but not limited to the following working condition:

front-end position verification: the so-called front-end position means that when one grating blade in one of the two groups of grating blades is at the initial position, the position of the end face, close to one side of the middle position, i.e., the end surface of the free end, of the grating blade is a front-end position of a grating blade corresponding to the grating blade in the other group of grating blades, i.e., an extreme position at which one grating blade can move forward; the front-end position verification method comprises the steps of arranging front-end position sensors at the front ends, i.e., the free ends, of the grating blades, driving single grating blades in one group of grating blades or in the other group at the position corresponding to the grating blades to be verified to return to the initial position first, then moving the first grating blade to be verified to the front-end position till triggering the front-end position sensor, marking the front-end position to complete the front-end position verification of the first grating blade, and then verifying the front-end position of the second grating blade according to the same program till completing the front-end position verification of all the grating blades.

Further, the control method also comprises but not limited to the following working condition:

moving speed verification of the grating blades or parameter verification of the motor, comprising the following steps: step 1, completing the initial position verification and the middle position verification, and obtaining the distance L between the initial position and the middle position as known or actually measured; step 2, driving one grating blade to move from the initial position to the middle position or from the middle position to the initial position, and recording the running time T or the motor revolution number S; and step 3, comparing the measured running time T or motor revolution number S with the previously stored running time T or motor revolution number S, if they are the same, prompting they are the same, and if they are different, executing at least one of the following steps: 1) prompting they are different, 2) repeating the above steps after adjustment or maintenance, and 3) storing the newly measured running time T or motor revolution number S, and incorporating the newly measured running time T or motor revolution number S into the technical formula $l=Lt/T$ or $l=Ls/S$ of the real-time position instead of the original parameters.

In practical application, the front-end position controller may also adopt the following solution, e.g., front-end position sensors matched with each other are respectively arranged at the front end, i.e., the free end, of each grating blade and the position corresponding to the middle line in the grating device, and the front-end position sensors are triggered when the front end of one grating blade arrives at the middle line. In this case, one of the two groups of grating blades of the grating device can run to the middle line, then the other group of grating blades can be verified one by one, the other group of grating blades runs to the middle line after verification, and then the remaining group of grating blades is verified. Or, one grating blade runs to the middle line, then a grating blade opposite to the grating blade is verified, and all the grating blades are verified one by one according to this method. In practical application, the front ends of the grating blades can be bored, the sensors are installed into the holes, and when the corresponding grating blades touch each other, the group of sensors is triggered.

Or, a transverse through-hole is formed in the front end of each grating blade of the grating device, a moving part of the front-end position sensor is arranged in the through-hole, a fixed part of the front-end position sensor is arranged on a grating blade support on one side or two sides of the grating blades, and when the moving part and the fixed part of the front-end position sensor on one grating blade are located on the same straight line and trigger the front-end position sensor, the front end of the grating blade is just located on the middle line.

Figure 3:
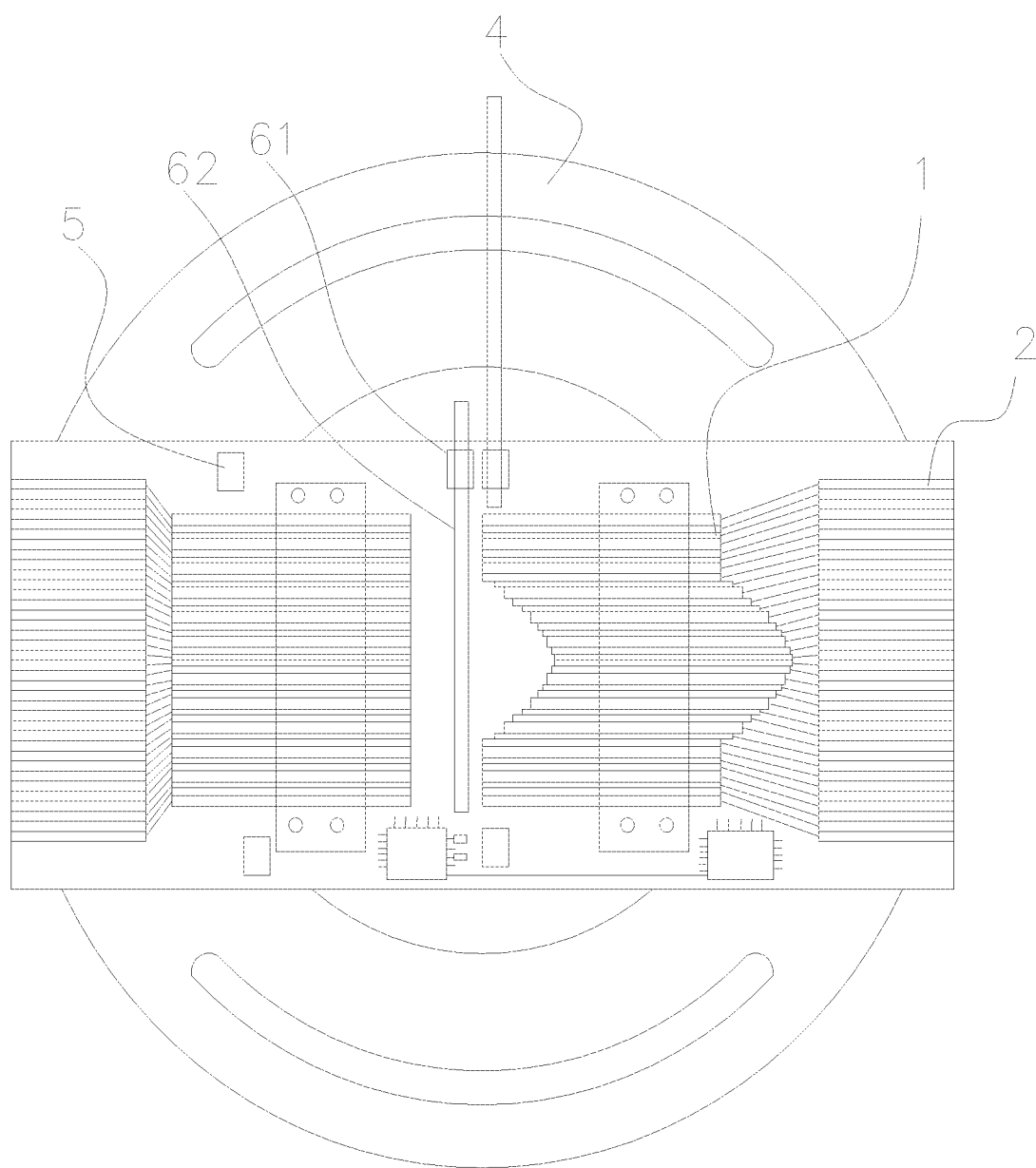
FIG. 3 is a schematic diagram of one embodiment of the present invention.

In order to reduce the cost, the following simple solution may also be adopted: as shown in FIG. 3, a front-end position controller is arranged on the support of the grating device, and the front-end position controller comprises:

a driving part 61, which is arranged on a grating body and drives limiting rods to stretch and contract horizontally;

two limiting rods 62, which can independently horizontally stretch and contract along the middle line and respectively correspond to the two groups of grating blades of the grating device, e.g., when a left grating blade is to be verified, the right limiting rod is driven to move to a movable area of the grating blades, substantially, the limiting rod is located on the other side of the middle line, so that the front end of the front-end position sensor is located on the middle line, and when the grating blade moves to the middle line and arrives at the middle line, the front-end position sensor corresponding to the blade is triggered; the other limiting rod corresponds to the other group of grating blades, and the working principle is same. and Front-end position sensors are arranged on the limiting rods 62 and face one side of the front ends of the grating blades, wherein after the limiting rods 62 completely move to the work area of the grating blades, the front-end position sensors correspond to all the grating blades one by one; after one grating blade touches the front-end position sensor corresponding thereto, the front-end position sensor is triggered, and the front end of the grating blade is located on the middle line at the moment.

In order to reduce the length of a single limiting rod 62, four limiting rods can be arranged in pair on two sides, and each pair of limiting rods is combined together to form a long limiting rod.

By adopting the solution, the structure of the grating device is simple; the grating blades do not need to be changed, so that the manufacturing cost is low; and one group of grating blades can be verified simultaneously or one working blade can be verified separately, so that the efficiency is higher.

The present invention further provides radiotherapy equipment, comprising a large frame and an accelerator arranged on the large frame, and also comprising the above-mentioned grating device, as shown in FIG. 2.

Described above are merely preferred embodiments of the present invention. It should be pointed out that many modifications and improvements can also be made for those of ordinary skill in the art without departing from the concept of the present invention. These modifications and improvements shall fall into the protection scope of the present invention.

The invention claimed is:

1. A grating device for radiotherapy equipment, comprising grating blades and a driving device thereof, and further comprising:
    a tail-end position controller, used for monitoring whether the tail ends of the grating blades arrive at a preset zero position, i.e., an initial position;
    a front-end position controller, used for monitoring whether the front ends of the grating blades arrive at a middle position, wherein when the two groups of grating blades are at the initial position, the front-end projections of the two groups of grating blades are two parallel straight lines, and the middle position is a straight line equidistant from the front ends of the two groups of grating blades; and
    a central controller, connected with the driving device, the tail-end position controller and the front-end position controller respectively;
    wherein the tail-end position controller and the front-end position controller verify the initial position and the middle position of one of the grating blades to obtain a distance between the initial position and the middle position of the one of the grating blades, wherein the driving device drives the one of the grating blades to move from the initial position to the middle position, and the central controller records a running time or a motor revolution number when the one of the grating blades moves from the initial position to the middle position.

2. The grating device for radiotherapy equipment according to claim 1, wherein the central controller receives data transmitted from the tail-end position controller and the front-end position controller, makes a judgment hereby and sends a control instruction to the driving device, and the driving device controls the grating blades to move or stop.

3. The grating device for radiotherapy equipment according to claim 2, wherein front-end position sensors are arranged at the front ends, i.e., the free ends, of the grating blades, and the front-end position sensors are triggered when the front ends of the two corresponding grating blades in the two groups of grating blades touch each other.

4. The grating device for radiotherapy equipment according to claim 2, wherein front-end position sensors matched with each other are respectively arranged at the front end, i.e., the free end, of each grating blade and a position corresponding to a middle line in the grating device, and the front-end position sensors are triggered when the front end of one grating blade arrives at the middle line.

5. The grating device for radiotherapy equipment according to claim 4, wherein a transverse through-hole is formed in the front end of each grating blade of the grating device, a moving part of the front-end position sensor is arranged in the through-hole, a fixed part of the front-end position sensor is arranged on a grating blade support on one side or two sides of the grating blade, and when the moving part and the fixed part of the front-end position sensor on one grating blade are located on the same straight line and trigger the front-end position sensor, the front end of the grating blade is just located on the middle line.

6. The grating device for radiotherapy equipment according to claim 1, wherein the front-end position controller comprises:
    a driving part, which is arranged on a grating body and drives limiting rods to stretch and contract horizontally;
    two limiting rods, which can independently horizontally stretch and contract along the middle line and respectively correspond to the two groups of grating blades of the grating device; and
    front-end position sensors, which are arranged on the limiting rods and face one side of the front ends of the grating blades, wherein after the limiting rods completely move to a work area of the grating blades, the front-end position sensors correspond to all the grating blades one by one; after one grating blade touches the front-end position sensor corresponding thereto, the front-end position sensor is triggered, and the front end of the grating blade is located on the middle line at the moment.

7. A control method for a grating device for radiotherapy equipment, comprising:
    verifying an initial position, when initial position sensors are independently arranged for each grating blade through a tail-end controller, the initial position of each grating blade is independently verified according to the detection data of each initial position sensor or control all or part of the grating blades to return to the initial position simultaneously or respectively; when only one initial position sensor is arranged for each group of grating blades, verifying the initial position comprises the steps of driving all the grating blades to leave from the initial position first, then moving the first grating blade which needs to be verified to the initial position till triggering the initial position sensor, marking the initial position to complete verifying the initial position of the first grating blade, driving the grating blade to leave from the initial position, and then verifying the initial position of the second grating blade according to the same program till completing verifying the initial position of all the grating blades;

verifying a middle position, comprising the steps of arranging a middle position sensor at the middle position as described in claim 1, driving all the grating blades to leave from the middle position first, then moving the first grating blade which needs to be verified to the middle position till triggering the middle position sensor, marking the middle position to complete verifying the middle position of the first grating blade, driving the grating blade to leave from the middle position, and then verifying the middle position of the second grating blade according to the same program till completing verifying the middle position of all the grating blades; and precisely positioning the grating blades, comprising steps of: step 1, completing verifying the initial position and verifying the middle position, and obtaining the distance L between the initial position and the middle position as known or actually measured; step 2, driving one grating blade to move from the initial position to the middle position or from the middle position to the initial position, and recording the running time T or the motor revolution number S; step 3, driving the grating blade to return to the initial position, and marking the initial position as zero at the moment; step 4, driving the grating blade to move from the initial position to the middle position, and simultaneously recording the time t or the revolution number s, the real-time position, i.e., actual moving distance, of the grating blade being 1=Lt/T or 1=Ls/S, and when 1 is equal to a preset value or a required value, the grating blade arriving at a target position and stopping moving.

8. The control method for the grating device for radiotherapy equipment according to claim 7, comprising:

verifying a front-end position, wherein the so-called front-end position means that when one grating blade in one of the two groups of grating blades is at the initial position, the position of the end face, close to one side of the middle position, i.e., the end surface of the free end, of the grating blade is a front-end position of a grating blade corresponding to the grating blade in the other group of grating blades, i.e., an extreme position at which one grating blade can move forward; verifying the front-end position comprises the steps of arranging front-end position sensors at the front ends, i.e., the free ends, of the grating blades, driving single grating blades in one group of grating blades or in the other group at the position corresponding to the grating blades to be verified to return to the initial position first, then moving the first grating blade which needs to be verified to the front-end position till triggering the front-end position sensor, marking the front-end position to complete verifying the front-end position of the first grating blade, and then verifying the front-end position of the second grating blade according to the same program till completing verifying the front-end position of all the grating blades.

9. The control method for the grating device for radiotherapy equipment according to claim 7, comprising:

verifying a moving speed of the grating blades or verifying parameter of the motor, comprising: step 1, completing verifying the initial position and verifying the middle position, and obtaining the distance L between the initial position and the middle position as known or actually measured; step 2, driving one grating blade to move from the initial position to the middle position or from the middle position to the initial position, and recording the running time T or the motor revolution number S; and step 3, comparing the measured running time T or motor revolution number S with the previously stored running time T or motor revolution number S, if they are the same, prompting they are the same, and if they are different, executing at least one of the following steps: 1) prompting they are different, 2) repeating the above steps after adjustment or maintenance, and 3) storing the newly measured running time T or motor revolution number S, and incorporating the newly measured running time T or motor revolution number S into the technical formula 1=Lt/T or 1=Ls/S of the real-time position instead of the original parameters.

10. A radiotherapy equipment, comprising a large frame and an accelerator arranged on the large frame, and further comprising the grating device of claim 1.

* * * * *